United States Patent [19]

Ehrhardt

[11] 4,187,423
[45] Feb. 5, 1978

[54] ARTICLE FOR MEASURING LOWER EXTREMITIES COMPRISING LAMINAE OF BOTH PVC AND ACRYLIC

[75] Inventor: Henry B. Ehrhardt, Arlington, Wash.

[73] Assignees: Larry C. Petersen; Stanley M. Smith, both of Marysville, Wash.

[21] Appl. No.: 890,296

[22] Filed: Mar. 27, 1978

[51] Int. Cl.² .......................... A61B 6/00; A61B 6/12
[52] U.S. Cl. ..................................... 250/312; 250/476
[58] Field of Search ............................... 250/476, 312

[56] References Cited

U.S. PATENT DOCUMENTS

| 2,141,193 | 12/1938 | Mott ...................................... 250/476 |
| 3,171,959 | 3/1965 | Kozek et al. .......................... 250/312 |

FOREIGN PATENT DOCUMENTS 205217  1/1968  U.S.S.R. .................................. 250/312

Primary Examiner—Alfred E. Smith
Assistant Examiner—T. N. Grigsby
Attorney, Agent, or Firm—Christie, Parker & Hale

[57] ABSTRACT

A method and apparatus designed and constructed to be used as an accessory on X-ray machines when making X-ray pictures on X-ray film of the lower extremities of the human body for the specific purpose of accurately measuring the long bones and the joint spacing. Also the analyzation and comparing of the long bones and joint spacings with each other.

The radiographic attachment apparatus is a separate unit from the X-ray machine and is not attached as a part thereof, but used as an accessory by merely placing the apparatus in the center of the X-ray table under the lower extremities of the body when making the X-ray pictures.

3 Claims, 5 Drawing Figures

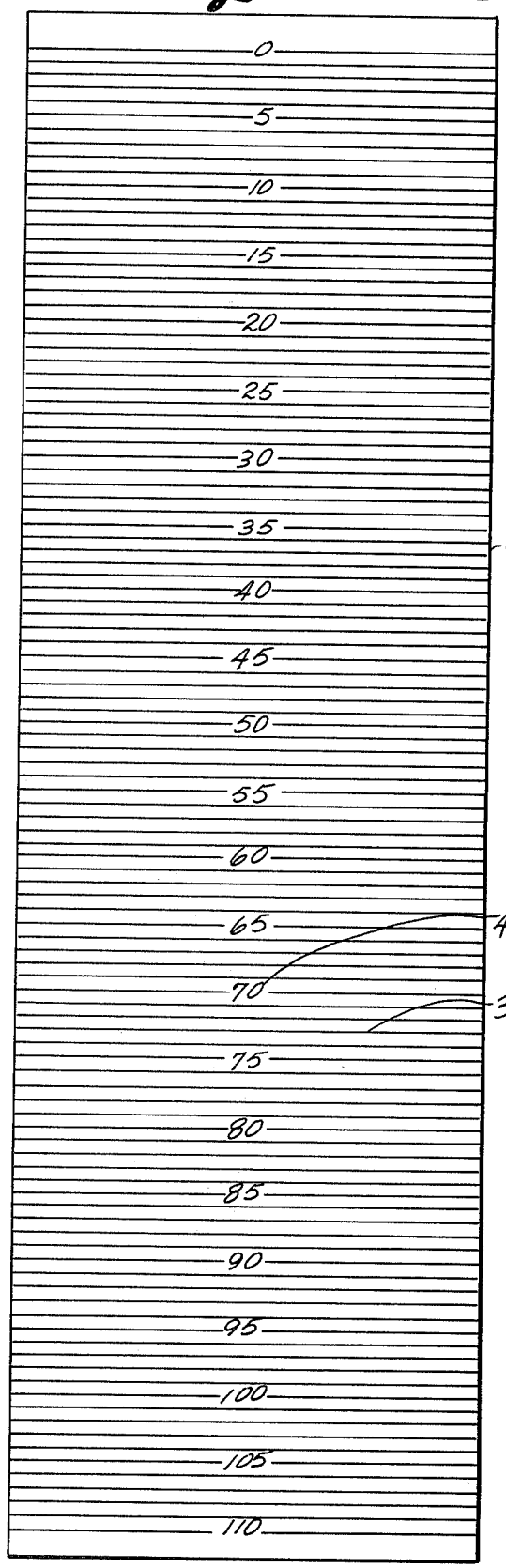
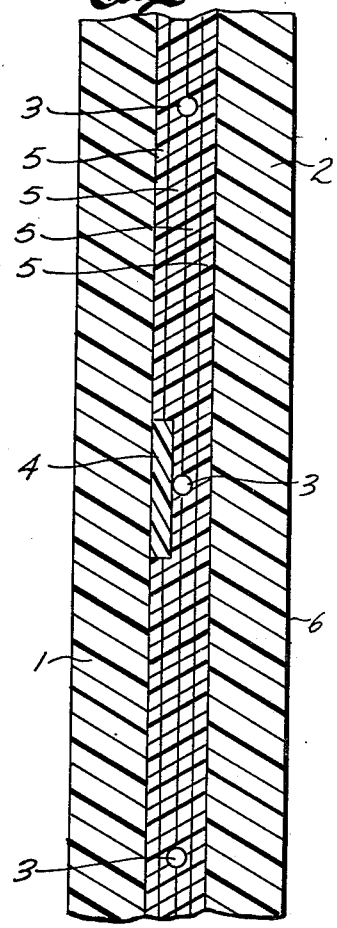
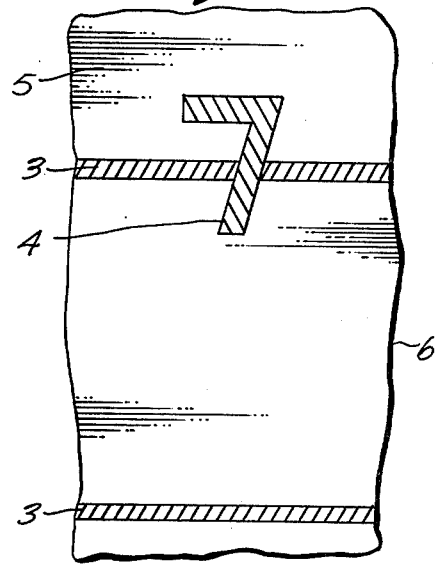

ARTICLE FOR MEASURING LOWER EXTREMITIES COMPRISING LAMINAE OF BOTH PVC AND ACRYLIC

BACKGROUND OF THE INVENTION

1. Field of the Invention

This invention relates generally to X-ray machines for the specific purpose of making X-ray pictures of the long bones and joints of the lower extremities of the human body with the addition of a superimposed image of the measuring cross lines and their identifying numbers in the same picture with the X-ray image of the long bones and joints of the lower extremities of the body.

This combination of images on the one film enables the doctor to scan the film and gain an accurate reading of the long bones and joints and also an accurate comparison of each to the other.

2. Description of the Prior Art

As far as I am aware the present means of measuring and comparing the long bones and joints of the lower extremities of the human body is to place a scale or rule under the patients lower extremities when making the X-ray pictures so that the image of the scale or the rule will be superimposed on the X-ray picture with that of the image of the long bones and joints. Then it is necessary to use added squares and other measuring instruments and place them adjacent to the rule image on the film and sliding them up or down to the desired position and place in order to take a measurement. This present method of measuring is inaccurate and very time consuming.

SUMMARY OF THE INVENTION

The present invention comprises of a radiographic attachment apparatus for comparative measuring of the lower extremities. Being a structure having a front and back panel made of acrylic sheet plastic laminated together with polyvinyl chloride sheets and copper wires running transversely across and in the middle of the laminations spaced one centimeter apart and numbered in increments of five, having lead or copper numbers placed over the center of the cross wires. The lamination is done with heat and pressure bonding the plastic, vinyl, wires and numbers into a hermetically sealed unit. The radiographic attachment apparatus is approximately three hundred thousandths of an inch thick, fourteen inches wide and forty-six inches long, having one hundred and ten transverse cross lines spaced one centimeter apart and properly numbered.

OBJECT AND ADVANTAGES OF THE INVENTION

It is an object of the invention to provide an accurate and dependable measuring attachment apparatus for X-ray use in determining the length of the long bones of the body and their respective joint spacing which can be immediately read by the doctor with complete confidence as to the accuracy and no waste of time.

It is still another object of this invention to provide an X-ray attachment comparative measuring apparatus for the analyzation and comparing of the long bones and joints spacing of the lower extremities.

It is still another object of this invention to provide an X-ray measuring attachment apparatus which is quick and simple to place on the X-ray table, safe and easily cleaned and kept sterile.

It is still another object of this invention to provide an X-ray measuring attachment apparatus with all needed and usable measurements incorporated into one single unit which is hermetically sealed resulting in a safe and accurate instrument to use. There is no need of the use of any additional measuring equipment in any manner.

The construction of this X-ray measuring attachment apparatus being of very substantial and durable material will last indefinitely with proper care and there is nothing to wear out, need replacement or get out of adjustment. It can be easily stored and kept sterile by merely wiping it off with a disinfectant cloth, there are no openings or areas which can harbor any contamination.

BRIEF DESCRIPTION OF THE DRAWINGS

Referring to the drawings, which are for illustrative purpose only and illustrate the techniques for accomplishing the invention but it is understood that the steps and apparatus may be modified within the intent and scope of the invention as defined.

FIG. 1 is a face elevation view of the radiographic attachment apparatus embodying the 110 transverse lines and their respective numbers;

FIG. 2 is a side edge elevation view;

FIG. 3 is a cross-sectional view of FIG. 2 of a blown up size through a number area which shows each part in their respective place and relation to each other;

FIG. 4 is a face view of FIG. 1 of a blown up size showing a small area of a lead number and its respective relation to the copper transverse wires;

DETAILED DESCRIPTION

Figure 5:
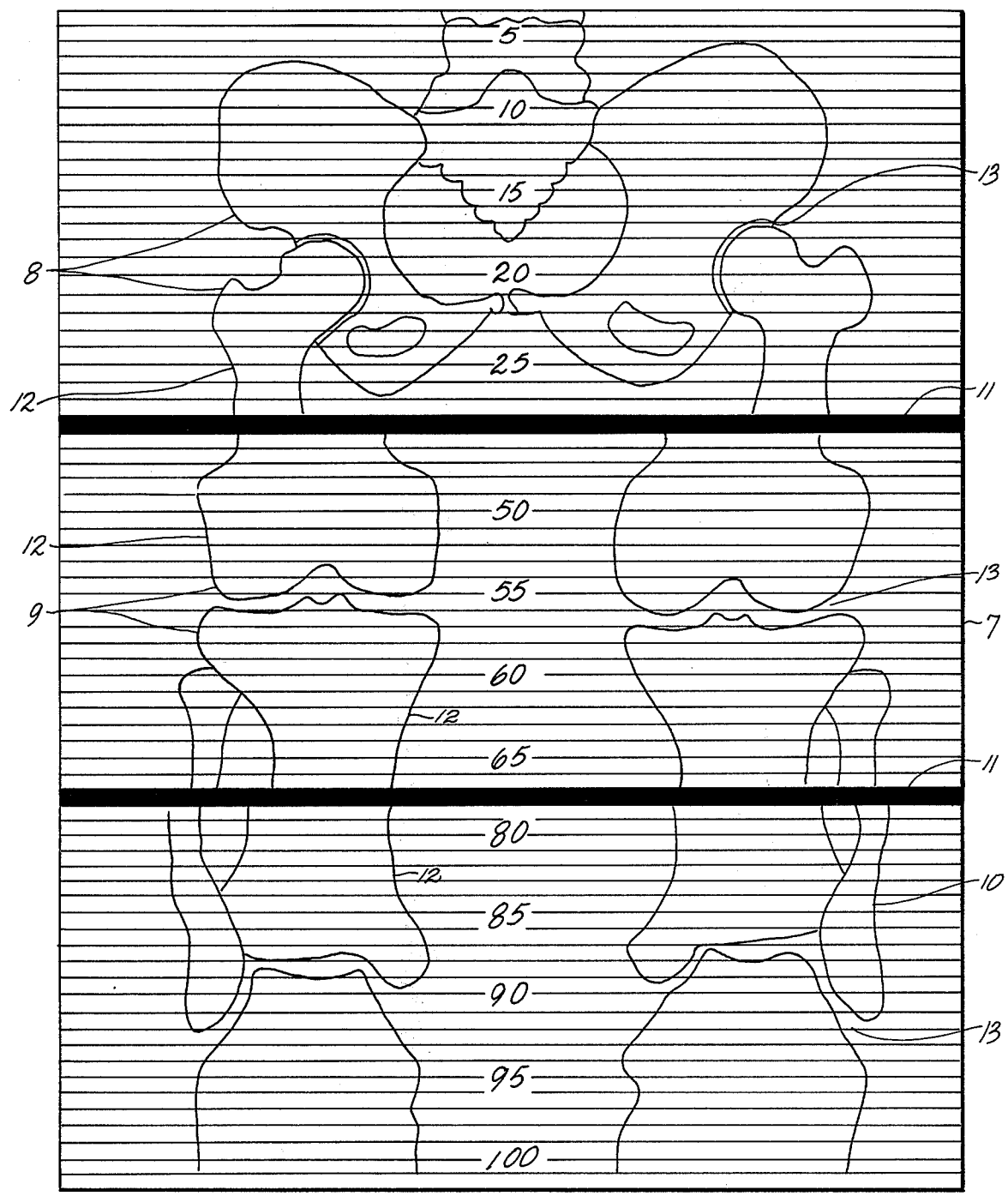
FIG. 5 is a facsimile drawing of an X-ray film picturing the pelvic area on the upper portion of the film, the knee area on the center portion of the film, and the ankle area on the lower portion of the film. All areas are on one 14"×17" X-ray film.

As shown in FIG. 1, the Radiographic Attachment Apparatus 6 designed to aid in the measuring of the long bones 12 and their respective joint spacing 13 of the lower extremities, consists of one hundred and ten cross lines 3 and their respective numbers 4 that are radiopaque with transverse wires 3 being spaced in increments of one centimeter and every five centimeters having a number 4. The apparatus 6 measures fourteen inches wide and forty-six inches long and subdivided into one centimeter segments by the cross lines 3.

As shown in FIG. 2, the Radiographic Attachment Apparatus 6 is approximately three hundred thousandths of an inch thick and forty-six inches long.

As shown in FIG. 3, the Radiographic Attachment Apparatus 6 is made of acrylic sheet plastic used as a back panel 2, with two sheets of laminating polyvinyl chloride sheets 5, placed on top of back panel 2. The transverse copper wires 3 are placed on top of sheets 5 parallel and one centimeter apart with there being one hundred and ten cross wires 3. The number 4 being of lead or cooper are placed on top of cross wires 3 in increments of every five centimeters. Then two additional sheets of laminating polyvinyl chloride sheets 5 are placed on top of the numbers 4 and cross wires 3 with a front panel 1 being added last and made of acrylic sheet plastic. The Apparatus 6 is then fused together into a hermetically sealed unit by heat and pressure. The polyvinyl chloride has a lower working temperature which allows it to bond to the acrylic and it is also soft and the numbers and wires will imbed themselves into it when heat and pressure are applied. The acrylic is what gives the apparatus its hard smooth outer finish and it will not bond together without the thin sheets of polyvinyl chloride between them.

As shown in FIG. 4, the Radiographic Attachment Apparatus 6 has numbers 4 which are placed over and centered on cross lines 3. A number 4 is placed over every fifth cross line 3.

As shown in FIG. 5, the standard fourteen inch by seventeen inch X-ray film 7 has superimposing of the transverse cross lines 3 which are one centimeter apart and the identifying numbers 4 in image on the X-ray film 7 with the X-ray image of the long bones 12 and their respective joint spacing 13. The X-ray film 7 is divided into three equal portions of five and two thirds inch length (two end portions and one central portion) parts by the overlap lead shielding image 11 which occurs in the middle sections of the long bones 12, causing the middle sections of the long bones 12 not to show up on the X-ray film 7. The length of the long bones 12 are known by counting numbers 4 and cross lines 3 on X-ray film 7 to determine their length. The missing segments do not affect the measurements because the patient and the apparatus 6 are not moved while taking the three X-ray exposures on the single X-ray film 7.

The Radiographic Attachment Apparatus 6, which serves as a marking sheet, is placed on the X-ray table (not shown) with the patient (not shown) on top of Apparatus 6 so that his pelvic area 8, knee area 9, ankle area 10 are positioned over the Apparatus 6. The X-ray film 7 is inserted into the X-ray machine under the Apparatus 6 in the ankle area 10 and the upper two thirds of film 7 (the upper end portion and central portion) is blocked out with lead plates, while exposing the lower end portion of film 7 to X-rays directed at the patient from above. The same X-ray film 7 is then inserted under knee area 9 and the upper end portion and the lower end portion of the same film 7 are blocked out with lead plates, while exposing the central portion of film 7 to X-rays directed at the patient from above. The same X-ray film 7 in finally inserted under the pelvic area 8 and the central portion and lower end portion of film 7 are blocked out with lead plates, while exposing the upper end portion of film 7 to X-rays directed at the patient from above. The X-ray film 7 is then developed to show the pelvic area image 8, knee area image 9, and ankle area image 10 all on the single fourteen by seventeen inch X-ray film 7. The length of and a comparison of the long bones 12 and the joint spacings 13 can be determined by reading the graduations, i.e., centimeter cross lines 3 and their respective numerical symbols, i.e., numbers 4 which are superimposed on X-ray picture 7 and easily and immediately read without any computations. Of course, the order of exposure of the portions of film 7 and the lower body areas could be different.

The patient and the attachment apparatus are stationary on the X-ray table. They do not move while the three pictures are being taken. Only the one film is used and it is moved under the patient to the three joint locations. Only one third of this film is being exposed with each picture. The masking off of the negative with lead plates, allows only the desired portion to be exposed. When the X-ray film is developed it will have sections of numbers missing, but due to the 14"×46" apparatus having lines and numbers spaced by centimeters from the top to the bottom, you can read your measurements and spacings off the 14"×17" X-ray picture. The X-ray picture on film is not reduced in size, the bones are full size, but the middle sections of the long bones do not show on the picture.

I claim:

1. A lower extremity measuring article having a suitable surface area for a person to lay on, and permeable to X-ray with imbedded numerals and wires nonpermeable to X-ray used between a source of X-ray and X-ray film so as to produce a permanent image of numbered and parallel spaced lines on the film, the spacing of which corresponds to the measurements of a system of length, the article being made of acrylic plastic and polyvinyl chloride layers nonopaque to X-ray, and the numerals and wires being disposed between said layers and fused together under heat and pressure to form a laminated hermetically sealed structure nontoxic to humans and easily sterilized.

2. The article of claim 1, in which the numerals and wires are imbedded in the polyvinyl chloride layer and the acrylic plastic layer encloses the polyvinyl chloride layer.

3. The article of claim 1, in which the numerals and wires are imbedded in the polyvinyl chloride layer and the acrylic plastic layer comprises a first sheet fused to one side of the polyvinyl chloride layer and a second sheet fused to the other side of the polyvinyl chloride layer.

* * * * *